United States Patent
Suzuki et al.

(10) Patent No.: US 10,876,086 B2
(45) Date of Patent: Dec. 29, 2020

(54) CELL TREATMENT METHOD, LASER PROCESSING MACHINE, AND CELL CULTURE VESSEL

(71) Applicants: KATAOKA CORPORATION, Kyoto (JP); NATIONAL INSTITUTE OF ADVANCED INDUSTRIAL SCIENCE AND TECHNOLOGY, Tokyo (JP)

(72) Inventors: Masami Suzuki, Kyoto (JP); Norio Nishi, Kyoto (JP); Junichi Matsumoto, Kyoto (JP); Kimio Sumaru, Tsukuba (JP); Toshiyuki Kanamori, Tsukuba (JP)

(73) Assignees: KATAOKA CORPORATION, Kyoto (JP); NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 185 days.

(21) Appl. No.: 15/576,228

(22) PCT Filed: Mar. 25, 2016

(86) PCT No.: PCT/JP2016/059769
§ 371 (c)(1),
(2) Date: Nov. 21, 2017

(87) PCT Pub. No.: WO2016/194454
PCT Pub. Date: Dec. 8, 2016

(65) Prior Publication Data
US 2018/0142193 A1 May 24, 2018

(30) Foreign Application Priority Data
Jun. 1, 2015 (JP) ................................. 2015-111759

(51) Int. Cl.
| | |
|---|---|
| C12M 1/42 | (2006.01) |
| C12N 1/00 | (2006.01) |
| C12M 1/00 | (2006.01) |
| C12M 1/34 | (2006.01) |
| C12M 1/32 | (2006.01) |
| C12M 1/26 | (2006.01) |
| C12N 1/02 | (2006.01) |
| C12N 5/00 | (2006.01) |
| C12N 13/00 | (2006.01) |
| C12M 1/12 | (2006.01) |

(52) U.S. Cl.
CPC .............. *C12M 1/42* (2013.01); *C12M 1/005* (2013.01); *C12M 1/3446* (2013.01); *C12M 23/20* (2013.01); *C12M 25/06* (2013.01); *C12M 31/02* (2013.01); *C12M 33/06* (2013.01); *C12M 33/10* (2013.01); *C12M 47/04* (2013.01); *C12N 1/00* (2013.01); *C12N 1/02* (2013.01); *C12N 5/0081* (2013.01); *C12N 13/00* (2013.01)

(58) Field of Classification Search
None
See application file for complete search history.

(56) References Cited

U.S. PATENT DOCUMENTS

| | | | | |
|---|---|---|---|---|
| 4,624,915 A * | 11/1986 | Schindler | ................ | B07C 5/342 |
| | | | | 435/286.2 |
| 4,629,687 A * | 12/1986 | Schindler | ................ | B07C 5/342 |
| | | | | 435/286.2 |
| 5,618,654 A * | 4/1997 | Takei | .................... | G02F 1/0126 |
| | | | | 430/347 |
| 2003/0148393 A1* | 8/2003 | Woodbury | ......... | G01N 21/6408 |
| | | | | 435/7.2 |
| 2005/0276456 A1* | 12/2005 | Yamato | ................ | G02B 21/365 |
| | | | | 382/128 |
| 2008/0057558 A1* | 3/2008 | Niwa | ................. | G02B 21/0088 |
| | | | | 435/173.9 |
| 2010/0055759 A1 | 3/2010 | Blau et al. | | |
| 2013/0023025 A1* | 1/2013 | Sumaru | .................. | C12M 23/20 |
| | | | | 435/173.9 |

(Continued)

FOREIGN PATENT DOCUMENTS

| | | |
|---|---|---|
| EP | 2 554 657 S1 | 2/2013 |
| EP | 3 315 600 A1 | 5/2018 |
| JP | 2003-339373 A | 12/2003 |

(Continued)

OTHER PUBLICATIONS

Kojima, et al., "Photothermogenic Properties of Different-Sized Gold Nanoparticles for Application to Photothermal Therapy", 2014, The Chemical Society of Japan, Chem.Lett. 2015, vol. 43, pp. 975-976.

(Continued)

*Primary Examiner* — Louise W Humphrey
*Assistant Examiner* — Srikanth Patury
(74) *Attorney, Agent, or Firm* — McGinn IP Law Group, PLLC

(57) ABSTRACT

A method of killing specific cells from among a group of cells cultured in a culture vessel by quick and brief laser treatment, the cell culture vessel comprising a main body and a to-be-irradiated layer attached to the main body, the to-be-irradiated layer containing an ingredient capable of absorbing laser light upon laser irradiation, the group of cells being cultured on the surface of the to-be-irradiated layer, the method comprising:
applying laser light to a partial area of the to-be-irradiated layer directly below the specific cells.

13 Claims, 12 Drawing Sheets

(56) References Cited

U.S. PATENT DOCUMENTS

2015/0044770 A1* 2/2015 Kim .................. C12M 23/20
435/377

FOREIGN PATENT DOCUMENTS

| JP | 2005-333889 A | | 12/2005 |
|----|---------------|---|---------|
| JP | 2012-023970 A | | 2/2012 |
| WO | WO 2004/037968 | * | 5/2004 |
| WO | WO 2011/125615 A1 | | 10/2011 |

OTHER PUBLICATIONS http://chem.rice.edu/ShowInterior.aspx?id=154.
V. Ziegler et al., "Photosensitizer Adhered to Cell Culture Microplates Induces Phototoxicity in Carcinoma Cells", BioMed Research International, Hindawi Publishing Corporation, vol. 2013, Article ID 549498, 11 pages, (Jan. 1, 2013).
European Search Report dated Nov. 6, 2018 for European Patent Application No. 16802892.6-111/3305888 PCT/JP2016059769.
International Search Report (ISR) (PCT Form PCT/ISA/210), in PCT/JP2016/059769, dated Jun. 14, 2016.
http://cben.rice.edu/ShowInterior.aspx?id=154 (1 page of home page), 2007.
European Office Action dated Mar. 23, 2020 in European Application No. 16 802 892.6.
European Office Action dated Aug. 22, 2019 in European Application No. 16 802 892.6.
European Office Action dated Oct. 7, 2020 in European Application No. 16 802 892.6.
Lee, et al., "Azo Polymer Multilayer Films b Electrostatic Self-Assembly and Layer-by-Layer Post Azo Functionalization", American Chemical Society, 2000, pp. 6534-6540.

* cited by examiner

CELL TREATMENT METHOD, LASER PROCESSING MACHINE, AND CELL CULTURE VESSEL

FIELD

The present invention relates to a method of killing specific cells from among a group of cells cultured in a cell culture vessel, and to a laser processing machine and a cell culture vessel for use in the method.

BACKGROUND

Recently, fast growth has been witnessed in researches and developments of regenerative therapy technology and researches in drug discovery with the use of somatic stem cells, embryonic stem cells, induced pluripotent stem cells, and induced pluripotent stem cells. In these researches and developments, it is crucial to be able to produce desired cells and tissues in a large amount with high efficiency.

The process of cell culturing normally includes subculturing, which refers to the procedure of taking a cell clump out of a cell assembly (colony) that has proliferated in a culture medium and then transferring the cell clump to a fresh culture medium for another round of proliferation. Currently, dividing a proliferated colony into multiple clumps relies exclusively on manual operation. However, the dividing operation takes time and work and can cause irregularities in the size of the clumps, which can result in variations in the state of growth of the subcultured cells.

In regenerative therapy, cells or tissues to be transplanted for replacing or regenerating damaged tissues or organs of a patient should not contain any cells that remain after having failed to properly differentiate, otherwise these unwanted cells can cause harm to the patient's health (by inducing tumorigenesis, for example). Discarding a whole culture vessel contaminated with unwanted cells decreases the yield (the rate of harvesting) of desired cells or tissues, making regenerative therapy very expensive. In order to increase the yield of desired cells or tissues, it is desirable to kill or remove unwanted cells present in a culture vessel and thereby avoid wasting the other cells.

Patent Literature 1 discloses a method of selectively killing unwanted cells present in a culture vessel. More specifically, this method comprises coating the surface of a culture vessel in advance with a photoacid generator (which generates an acidic substance upon irradiation with an active energy ray, such as a ray of visible light, ultraviolet light, infrared light, or radiation), culturing cells in the culture vessel, conducting irradiation with active energy rays for about 10 seconds to about 10 minutes on a specific area where cells to be killed are present, and thereby inducing generation of acidic substances to kill the cells. For controlling the active energy rays to irradiate only a certain area, a device such as a DMD (digital micromirror device), a liquid-crystal shutter array, a spatial light modulator element, or a photomask is used.

The method disclosed in Patent Literature 1, however, takes a long time to kill target cells by irradiation with active energy rays. For this reason, this method has room for improvement in order to produce a large amount of cells to be required in the near future for regenerative therapy. And, this method has more problems: a microprojection system equipped with a device like a DMD wastes most of the active energy from the source (light source); and it is difficult to maintain a uniform distribution of intensity of the active energy rays irradiating the photoacid generator.

In this method, direct irradiation with high-energy active energy rays such as pulsed laser rays can be adopted for quickly killing unwanted cells. However, it is necessary for the active energy rays to hit the cell nuclei and therefore multiple irradiations are required to kill all target cells. This method has yet another, fundamental problem. That is, heat of the active energy rays inevitably affects other cells near the directly irradiated, unwanted cells.

CITATION LIST

Patent Literature

Patent Literature 1: International Publication No. WO 2011/125615

SUMMARY

Technical Problem

An object of the present invention is to kill specific cells from among a group of cells cultured in a culture vessel by quick and brief laser treatment.

Solution to Problem

A cell treatment method according to the present invention is a method of killing specific cells from among a group of cells cultured in a cell culture vessel, the cell culture vessel comprising a main body and a to-be-irradiated layer attached to the main body, the to-be-irradiated layer containing an ingredient capable of absorbing laser light upon laser irradiation, the group of cells being cultured on the surface of the to-be-irradiated layer, the method comprising:

applying laser light to a partial area of the to-be-irradiated layer directly below the specific cells.

In order to minimize the effect of heat on other cells near the specific cells, it is preferable that the laser light applied to the partial area of the to-be-irradiated layer directly below the specific cells have the right level of output or energy amount to kill the specific cells not instantly but after a certain period of time.

In order to minimize the effect of heat on other cells near the specific cells, it is also preferable that the laser light applied to the partial area of the to-be-irradiated layer directly below the specific cells have the right level of output or energy amount not to kill the specific cells instantly and be applied multiple times. In this case, the time period from laser irradiation to death of target cells can be shortened.

The cell treatment method according to the present invention can be used for dividing the group of cells (namely, a plurality of cells) cultured in the cell culture vessel into a plurality of portions. In this case, the laser light is applied to a partial area of the to-be-irradiated layer directly below the boundary between any two portions of the group of cells.

A laser processing machine according to the present invention is used for killing specific cells from among a group of cells cultured in a cell culture vessel, the cell culture vessel comprising a main body and a to-be-irradiated layer attached to the main body, the to-be-irradiated layer containing an ingredient capable of absorbing laser light upon laser irradiation, the group of cells being cultured on the surface of the to-be-irradiated layer, the laser processing machine being configured to:

apply laser light to a partial area of the to-be-irradiated layer directly below the specific cells.

It is particularly preferable for the laser processing machine that the laser light applied to the partial area of the to-be-irradiated layer directly below the specific cells have the right level of output or energy amount to kill the specific cells not instantly but after a certain period of time.

It is also preferable for the laser processing machine that the laser light applied to the partial area of the to-be-irradiated layer directly below the specific cells have the right level of output or energy amount not to kill the specific cells instantly and be applied multiple times.

The laser processing machine according to the present invention can be used for dividing the group of cells cultured in the cell culture vessel into a plurality of portions. The dividing is conducted by applying laser light to a partial area of the to-be-irradiated layer directly below the boundary between any two portions of the group of cells.

The cell culture vessel according to the present invention comprises a main body and a to-be-irradiated layer attached to the main body. The to-be-irradiated layer contains an ingredient capable of absorbing laser light upon laser irradiation. Cells are cultured on the surface of the to-be-irradiated layer.

Advantageous Effects of Invention

The present invention enables killing of specific cells from among a group of cells cultured in a culture vessel by quick and brief laser treatment.

DESCRIPTION OF EMBODIMENTS

Figure 1:
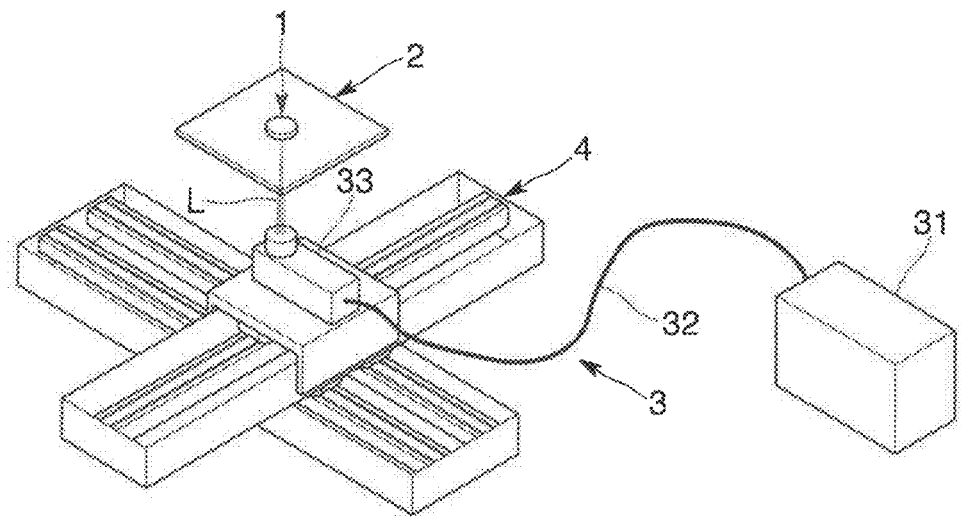
FIG. 1 is a schematic perspective view of a laser processing machine according to an embodiment of the present invention.

An embodiment of the present invention will be described referring to drawings. A laser processing machine according to this embodiment is configured to conduct laser treatment to kill specific cells from among a group of cells cultured on a cell culture vessel 1. Referring to FIG. 1, the laser processing machine principally consists of a support 2 supporting one or a plurality of cell culture vessels 1, a laser irradiator 3 configured to apply a laser beam L to the cell culture vessel 1 supported on the support 2, a displacement mechanism 4 configured to control the target location in the cell culture vessel 1 where the laser beam L is to be directed, and a control module 5 configured to control the laser irradiator 3 and the displacement mechanism 4.

It is preferable that the cell culture vessel 1 and the support 2 be disposed within a $CO_2$ incubator (not shown). The $CO_2$ incubator is a well-known device with its internal atmosphere being controllable in terms of $CO_2$ concentration and temperature. The $CO_2$ incubator is used in order to maintain a suitable cell-culturing environment, such as a suitable pH level of the culture medium in the cell culture vessel 1, during the laser treatment.

The laser irradiator 3 comprises a laser source 31, a processing nozzle 33 configured to discharge the laser light L emitted from the laser source 31 toward the cell culture vessel 1, and an optical system 32 disposed between the laser source 31 and the processing nozzle 33 and configured to transfer the laser light L from the laser source 31 to the processing nozzle 33.

The laser source 31 is a device configured to oscillate a continuous-wave laser or pulsed laser L (the pulsed laser may be a high-frequency laser having a pulse width similar to that of a continuous wave). The laser L is not limited in terms of wavelength but may be a visible-light laser having such a wavelength as 405 nm, 450 nm, 520 nm, 532 nm, or 808 nm or an infrared laser, for example. It is necessary that energy of the laser L having the selected wavelength be absorbed by a to-be-irradiated layer 12 (described below) of the cell culture vessel 1. An ultraviolet laser having a wavelength of 380 nm or lower may undergo absorption by a DNA or a protein, potentially affecting cells. So, it is preferable that the wavelength of the laser L be greater than 380 nm. In this embodiment, the laser source 31 emits a continuous-wave diode laser having a wavelength near 405 nm and a maximum output of 5 W.

The processing nozzle 33 is equipped with, for example, a built-in lens that gathers the laser light L prior to irradiation of the to-be-irradiated layer 12 of the cell culture vessel 1 as well as a shutter or a mirror that switches between ON and OFF of the emission of the laser light L. The processing nozzle 33 is disposed below the cell culture vessel 1 supported on the support 2 and discharges the laser L upward. The optical axis of the laser beam L discharged from the processing nozzle 33 entries into the to-be-irradiated layer 12 of the cell culture vessel 1 at a substantially right angle.

The optical system 32 for transferring the laser L from the laser source 31 to the processing nozzle 33 may consist of any optical components such as an optical fiber, a mirror, and a lens.

The displacement mechanism 4 principally consists of an XY stage configured to displace the processing nozzle 33 of the laser irradiator 3 relative to the cell culture vessel 1 supported on the support 2. The XY stage 4 is a known XY stage capable of quickly moving an object disposed on a linear-motor sliding platform or the like in the X-axis direction (leftward and rightward) and in the Y-axis direction (frontward and backward) with precision. In this embodiment, the processing nozzle 33 is supported on the XY stage 4 and the processing nozzle 33 is moved relative to the support 2 and the cell culture vessel 1. An alternative configuration may also be adopted where the support 2 is supported on the XY stage 4 and both the support 2 and the cell culture vessel 1 are moved relative to the processing nozzle 33. In either case, the displacement mechanism 4 allows displacement of the target location on the to-be-irradiated layer 12 of the cell culture vessel 1 where the laser L is to be directed while maintaining a substantially constant angle between the to-be-irradiated layer 12 of the cell culture vessel 1 and the optical axis of the laser beam L.

Figure 2:
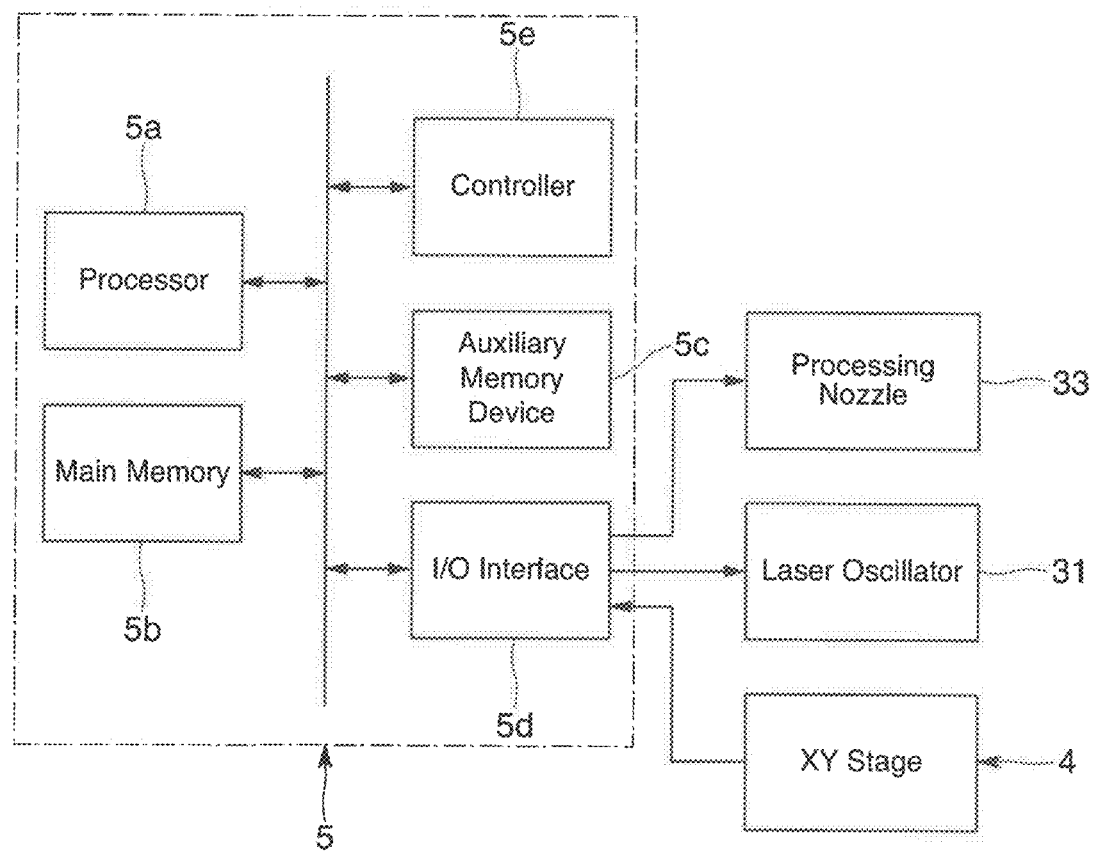
FIG. 2 is a diagram showing the configuration of hardware resources in the laser processing machine.

Referring to FIG. 2, the control module 5 consists of components such as a processor 5a, a main memory 5b, an auxiliary memory device 5c, a command-inputting device 5d, and an I/O interface 5e. Each of these components is controlled by a controller (such as a system controller or an I/O controller) to operate in coordination with the other components. The auxiliary memory device 5c is a flash memory or a hard drive, for example. The command-inputting device 5d is a device operable with a finger, such as a touch panel, a track pad, a pointing device like a mouse, a keyboard, or a push button. The I/O interface 5e may comprise a servo driver (servo controller). The control module 5 may consist of a general-purpose personal computer, a server computer, and a workstation, for example.

Figure 3:
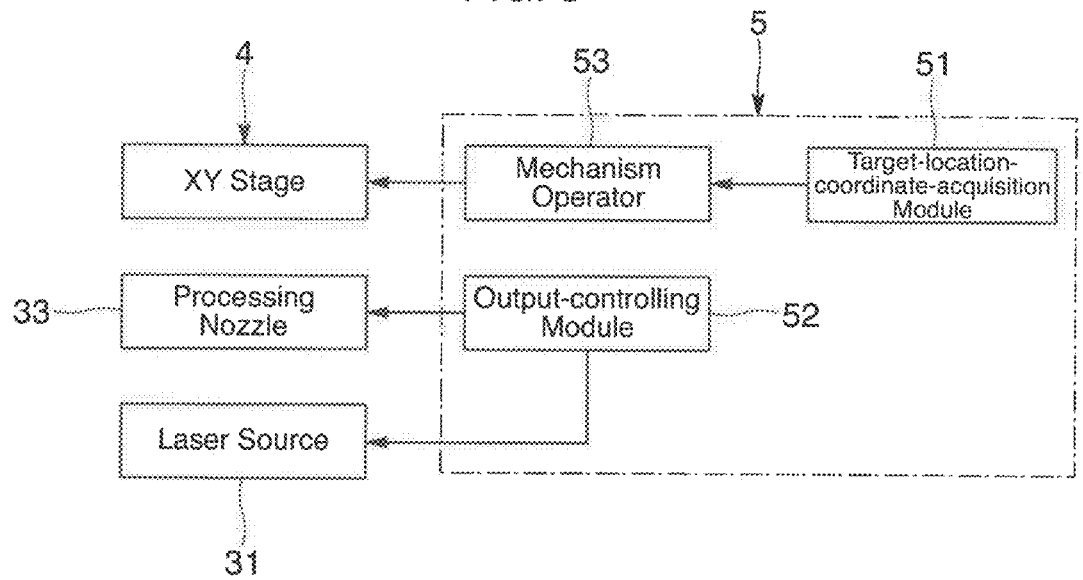
FIG. 3 is a functional block diagram of the laser processing machine.

The program to be run by the control module 5 is stored in the auxiliary memory device 5c. To run the program, the main memory 5b reads it and then the processor 5a interprets it. According to the program, the control module 5 functions as a target-location-coordinate-acquisition module 51, an output-controlling module 52, and a mechanism operator 53, as shown in FIG. 3.

The target-location-coordinate-acquisition module 51 is configured to acquire one or multiple sets of X-Y coordinates of the target location in the cell culture vessel 1 where the laser light L is to be directed. The X-Y coordinates herein are a set of coordinates of the position of the specific cells to kill from among the group of cells cultured in the cell culture vessel 1. The specific cells to kill refer to the following, for example: unwanted cells present together with cells or tissues to be cultured; or in the case where a cell colony in the cell culture vessel 1 is to be divided into a plurality of cell clumps for subculturing, cells on the boundary between the cell clumps. The information on the coordinates of the target location where the laser light L is to be directed may be stored in advance in the main memory 5b or the auxiliary memory device 5c, or the coordinates of the target location may be manually specified by a user. The target-location-coordinate-acquisition module 51 acquires the information on the coordinates of the target location by reading it from the main memory 5b or the auxiliary memory device 5c or by receiving a command specifying the coordinates of the target location from a user via the command-inputting device 5d.

The coordinates of the target location where the laser light L is to be directed may also be acquired as follows: an image of a cell colony in the cell culture vessel 1 is taken with a camera sensor such as a CCD or a CMOS; the resulting image is analyzed; and then the position of the unwanted cells or any other cells to kill is specified. Detection of the position of the cells to kill (more specifically, determination of the coordinates of the target location where the laser light L is to be directed) through image analysis may be conducted by the control module 5 itself or by an external device or computer (not shown) communicatively coupled to the control module 5. In the former case, the target-location-coordinate-acquisition module 51 acquires via the I/O interface 5e an image taken with the camera sensor and then analyzes the image to acquire the coordinates of the target location. In the latter case, the target-location-coordinate-acquisition module 51 receives the information on the coordinates of the target location from the external device or computer via the I/O interface 5e, thereby acquiring the coordinates of the target location.

The output-controlling module 52 is configured to control the ON-OFF state of the discharge of the laser L from the processing nozzle 33 toward the to-be-irradiated layer 12 of the cell culture vessel 1 and to control the output intensity of the laser L irradiating the to-be-irradiated layer 12, namely the amount of energy of the laser L. More specifically, the output-controlling module provides the processing nozzle 33 via the I/O interface 5e with a command signal for switching between ON and OFF of the discharge of the laser L from the processing nozzle 33 and also provides the processing nozzle 33 or the laser source 31 via the I/O interface 5e with a control signal for controlling the output of the laser L.

The mechanism operator 53 is configured to operate the XY stage 4 supporting the processing nozzle 33 so as to move the processing nozzle 33 toward the coordinates of the target location acquired by the target-location-coordinate-acquisition module 51, thereby directing the optical axis of the laser beam L discharged from the processing nozzle 33 to the coordinates of the target location. More specifically, the mechanism operator provides the XY stage 4 via the I/O interface 5e with a command signal related to the coordinates of the target location acquired by the target-location-coordinate-acquisition module 51. By discharging the continuous-wave laser L or the high-frequency pulsed laser L, which is almost like a continuous-wave laser, from the processing nozzle 33 while moving the processing nozzle 33 and thereby moving the laser beam L according to the coordinates of the target location that are changing with time, the target location where the laser L is to be directed can be continuously moved while the to-be-irradiated layer 12 of the cell culture vessel 1 is being irradiated.

An alternative procedure may also be adopted, which is conducted as follows: the processing nozzle 33 is moved relative to the cell culture vessel 1 in a fashion similar to raster scanning with the optical axis of the processing nozzle 33 moving across a certain region on (the to-be-irradiated layer 12 of) the cell culture vessel 1; and then when the optical axis of the processing nozzle 33 has reached directly below the specific cells to kill, the processing nozzle 33 discharges the laser L.

Figure 4:
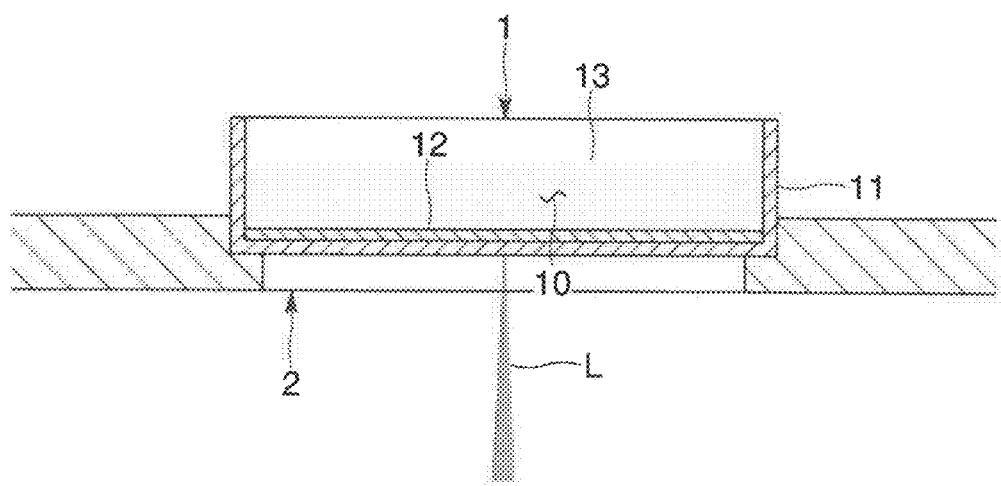
FIG. 4 is a sectional side view describing a cell treatment method according to the embodiment.

Referring to FIG. 4, the cell culture vessel 1 according to this embodiment comprises a main body 11 passable by the laser light L discharged from the processing nozzle 33 and the to-be-irradiated layer 12 attached to the main body. The to-be-irradiated layer contains a photoresponsive ingredient capable of generating heat and/or acid upon irradiation with the laser light L.

The main body 11 is made of a material, such as plastic or glass, that is transparent or light-transmissive to allow the passage of a light having a wavelength within the range of wavelength of the laser L discharged from the processing nozzle 33. Examples of the plastic include polystyrene polymers, acrylic polymers (such as poly(methyl methacrylate) (PMMA)), polyvinylpyridine polymers (such as poly(4-vinylpyridine) and 4-vinylpyridine-styrene copolymer), silicone polymers (such as polydimethylsiloxane), polyolefin polymers (such as polyethylene, polypropylene, and polymethylpentene), polyester polymers (such as poly(ethylene terephthalate) (PET) and poly(ethylene naphthalate) (PEN)), polycarbonate polymers, and epoxy polymers. The main body 11 may be a commercially-available culture vessel, which may be used as it is. In terms of shape, the main body 11 may be a dish (petri dish), a multidish, or a flask, for example, just like the shape of a commercially-available culture vessel.

Figure 5:
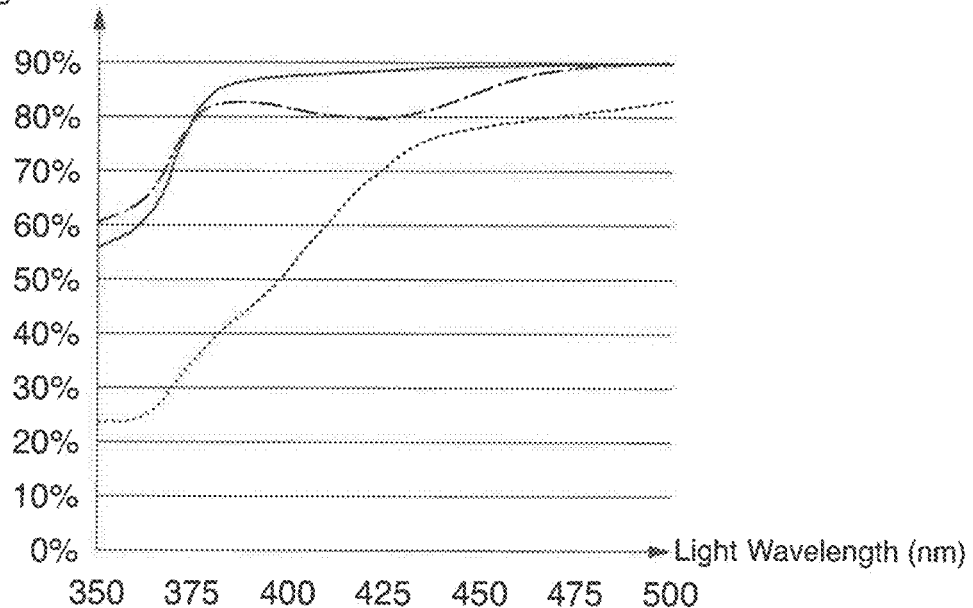
FIG. 5 comprises graphs that plot light transmittance and light absorbance, respectively. One of the graphs plots the light transmittance through a main body and a to-be-irradiated part of a cell culture vessel, and the other graph plots the light absorbance by the main body and the to-be-irradiated part.
Figure 5:
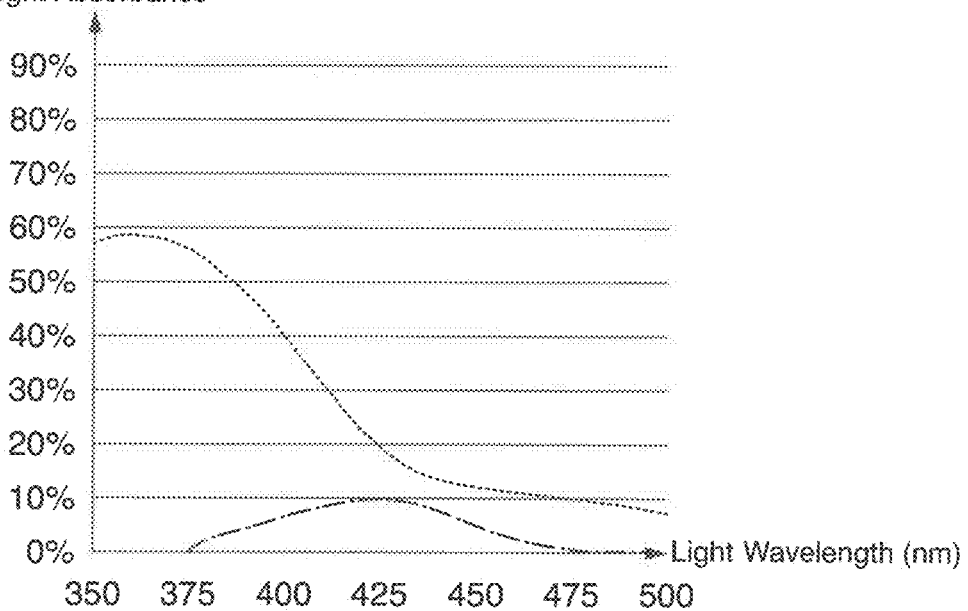

In FIG. 5, the light transmittance through the main body 11 is plotted with a solid line. The main body here is made of polystyrene resin and has a certain size and a certain shape. The light transmittance through the main body 11 is very high, as high as 85% or higher at a light wavelength of about 380 nm or greater. As the light wavelength decreases from a light wavelength of about 380 nm, the light transmittance decreases (in other words, the light absorbance by the main body 11 increases). This phenomenon is probably caused by impurities contained in the polystyrene material.

It is preferable that the to-be-irradiated layer 12 be made of a polymer (polymeric material) that contains a pigment structure (chromophore) capable of absorbing a light having a wavelength within the range of wavelength of the laser L discharged from the processing nozzle 33. This is because such a polymer can be easily applied to the main body 11 for coating, can ensure necessary adhesion of the cells, and tends not to enter into the cells. Examples of the pigment structure capable of absorbing the laser light L include derivatives of organic compounds such as azobenzene, diarylethene, spiropyrane, spirooxazines, fulgides, leucopigments, indigo, carotinoids (such as carotene), flavonoids (such as anthocyanin), and quinoids (such as anthraquinone). Examples of the polymer backbone include acrylic polymers, polystyrene polymers, polyolefin polymers, polyvinyl acetate, polyvinyl chloride, polyolefin polymers, polycarbonate polymers, and epoxy polymers.

Below is a specific example of the pigment-structure-containing polymer in the to-be-irradiated layer 12, poly[methylmethacrylate-co-(Disperse Yellow 7 methacrylate)] (Chemical 1, $(C_5H_8O_2)_m(C_{23}H_{20}N_4O_2)_n$). The azobenzene in this azo polymer may be unsubstituted azobenzene or one of various modified azobenzenes modified with a nitro group, an amino group, and/or a methyl group.

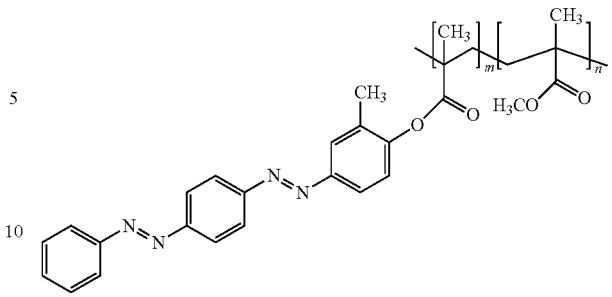

By applying a raw material liquid containing the pigment-structure-containing polymer described above or a raw material liquid containing the pigment-structure-containing polymer dissolved in a solvent (such as 1,2-dichloroethane or methanol) to the upward-facing surface of the main body 11, namely the bottom of a well 10, by spin coating, casting, or other techniques and then curing the raw material liquid, the to-be-irradiated layer 12 capable of generating heat upon irradiation with the laser light L can be formed. Alternatively, the main body 11 may be formed by using a material blend containing a pigment capable of absorbing the laser light L or by using the pigment-structure-containing polymer, and the resulting main body 11 has the function of the to-be-irradiated layer 12 capable of generating heat upon irradiation with the laser light L.

In FIG. 5, the light transmittance through and the light absorbance by the to-be-irradiated layer 12 are plotted with dashed lines. The to-be-irradiated layer here has a certain thickness and is made by coating the main body 11 with a polymer that contains azobenzene as the pigment structure. The light absorbance by the to-be-irradiated layer 12 reaches its peak at a light wavelength of about 360 nm and then decreases as the light wavelength increases from about 360 nm. Although the light absorbance by the to-be-irradiated layer 12 at a light wavelength of about 425 nm or greater is lower than 20%, there remains a certain level of light absorbance at great light wavelengths. This phenomenon indicates that the to-be-irradiated layer 12 is well capable of absorbing the laser light L having a wavelength of 405 nm, 450 nm, 520 nm, or 532 nm.

In addition to or instead of the pigment-structure-containing polymer described above, the to-be-irradiated layer 12 may comprise a photoacid generator capable of generating an acidic substance upon irradiation with the laser light L. As disclosed in Patent Literature 1, it is preferable that a photoacid generator contain a pigment structure (chromophore) capable of absorbing a light having a wavelength within the range of wavelength of the laser L discharged from the processing nozzle 33 and also contain an acid precursor to be broken down into an acidic substance. Examples of the photoacid generator include sulfonic acid derivatives, carboxylic acid esters, onium salts, and photoacid-generating groups having a nitrobenzaldehyde structure.

Specific examples of the sulfonic acid derivatives as the photoacid generator include thioxanthone-based sulfonic acid derivatives (such as 1,3,6-trioxo-3,6-dihydro-1H-11-thia-azacyclopenta[a]anthracen-2-yl sulfonate) and naphthaleneimide-based sulfonic acid derivatives (such as 1,8-naphthalimide sulfonate). In addition to these, sulfonic acid derivatives such as disulfones, disulfonyldiazomethanes, disulfonylmethanes, sulfonylbenzoylmethanes, imidesulfonates, and benzoinsulfonates may also be used.

Examples of the carboxylic acid esters include 1,8-naphthalenedicarboxylic imide methylsulfonate and 1,8-naphthalenedicarboxylic imide tosyl sulfonate. Examples of the onium salts include sulfonium salts and iodonium salts containing an anion, such as tetrafluoroborate ($BF_4^-$), hexafluorophosphate ($PF_6^-$), and hexafluoroantimonate ($SbF_6^-$).

By applying a raw material liquid containing a plastic (such as an acrylic polymer like PMMA or a polystyrene polymer, in particular) containing the photoacid generator or a raw material liquid containing the photoacid generator dissolved in a solvent (such as 1,2-dichloroethane or methanol) to the upward-facing surface of the main body 11, namely the bottom of the well 10, by spin coating, casting, or other techniques and then curing the raw material liquid, the to-be-irradiated layer 12 capable of generating heat and acid upon irradiation with the laser light L can be formed. Alternatively, the main body 11 may be formed by using a material blend containing the photoacid generator, and the resulting main body has the function of the to-be-irradiated layer 12 capable of generating heat and acid upon irradiation with the laser light L.

In FIG. 5, the light transmittance through and the light absorbance by the to-be-irradiated layer 12 are plotted with chain lines. The to-be-irradiated layer here has a certain thickness and is made by coating the main body 11 with a polymer that contains a thioxanthone-based sulfonic acid derivative having a thioxanthone backbone as the pigment structure and having a sulfonic acid as the acid precursor. The light absorbance by the to-be-irradiated layer 12 ranges from a light wavelength of about 375 nm to a light wavelength of about 460 nm. This means that a light having a wavelength outside this range is not absorbed by the to-be-irradiated layer 12 and the laser light L having a wavelength of 405 nm or 450 nm is absorbed by the to-be-irradiated layer 12. It should be noted that the light absorbance by this to-be-irradiated layer 12 is lower than the light absorbance (dashed line) by the to-be-irradiated layer 12 made by using a polymer that contains azobenzene as the pigment structure. In other words, the light absorbance by the to-be-irradiated layer 12 plotted with a chain line is lower than 20% (more specifically, even lower than 10%) at a visible-light wavelength ranging from about 400 nm to about 700 nm.

It is preferable that the material of the to-be-irradiated layer 12 generate no fluorescence upon irradiation with the laser light L. It is preferable that the thickness of the to-be-irradiated layer 12 be 10 μm or lower.

The surface of the to-be-irradiated layer 12 of the cell culture vessel 1 may be coated with an ingredient capable of enhancing cell adhesion, such as an ECM (extracellular matrix) like laminin or Matrigel.

For culturing cells, the well 10 formed in the main body 11 of the cell culture vessel 1 is filled with a culture medium (particularly, a liquid culture medium) 13. In other words, the culture medium 13 is positioned directly on the to-be-irradiated layer 12 disposed at the bottom of the well 10. The cells thus cultured adhere to and proliferate on the surface of the to-be-irradiated layer 12 and form cell colonies.

As shown in FIG. 4, the laser treatment for killing only unwanted cells from among a group of cells in the well 10 in the cell culture vessel 1 is conducted in the following way. The laser light L discharged from the processing nozzle 33 of the laser irradiator 3 is directed to a partial area of the to-be-irradiated layer 12 of the cell culture vessel 1 supported on the support 2 directly below the cells to kill. In this embodiment with the processing nozzle 33 disposed below the cell culture vessel 1, the laser light L that has been discharged upward from the processing nozzle 33 passes through the main body 11 to reach the to-be-irradiated layer 12 from the back side of the to-be-irradiated layer. The built-in lens in the processing nozzle 33 focuses or directs the laser light L discharged from the processing nozzle 33 to the to-be-irradiated layer 12 of the cell culture vessel 1. The partial area of the to-be-irradiated layer 12 irradiated with the laser light L absorbs energy of the laser light L and thereby generates heat and/or acid. This heat kills unwanted cells that are present directly above the partial area.

Figure 6:
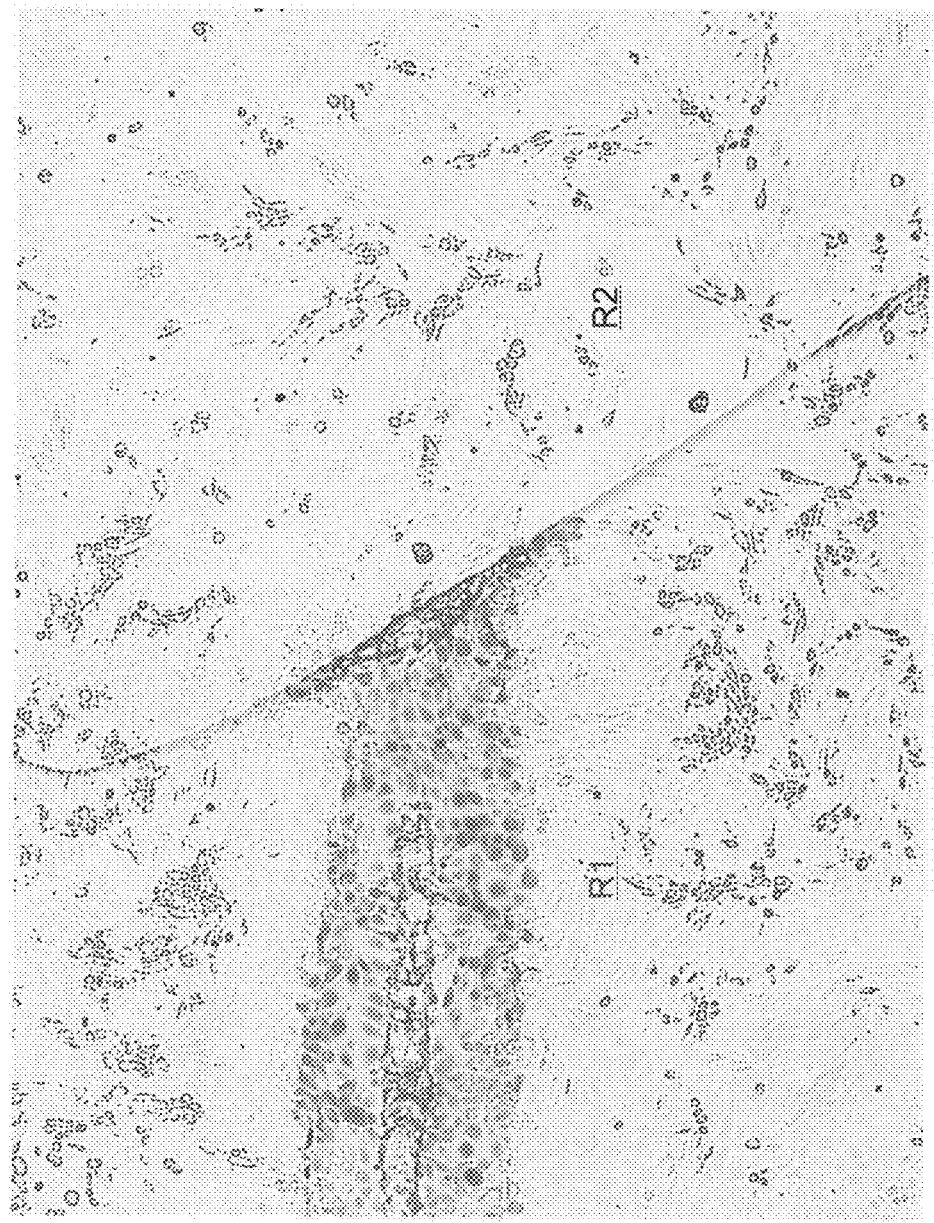
FIG. 6 is a photograph comparing the state of cells (death or survival) in the presence or absence of the to-be-irradiated part.

FIG. 6 shows the result of staining of dead cells with a trypan blue solution, which was conducted as follows: the upward-facing surface of the main body 11 of the cell culture vessel 1, namely the bottom of the well 10, was divided into a region R1 with the to-be-irradiated layer 12 and a region R2 without it; MDCK cells (Madin-Darby canine kidney cell) were cultured within the well 10; the bottom of the well 10 was irradiated with the continuous-wave laser L discharged from the processing nozzle 33 of the laser irradiator 3; and after the irradiation (namely, several hours after the irradiation), the cells were stained. The wavelength of the laser L was 405 nm, the output of the laser L was 5.08 W, and the diameter of the laser beam L was 50 μm. The processing nozzle 33 discharging the continuous-wave laser L, which practically corresponds to the laser beam L, was linearly moved once at a rate of 500 mm/second relative to the cell culture vessel 1. The partial area irradiated with the laser light L received energy (energy density) of the laser light L of about 25.9 $J/cm^2$ per unit area. The to-be-irradiated layer 12 comprised a polymer that contained azobenzene as the pigment structure.

FIG. 6 evidently shows the following: in the region R1 with the to-be-irradiated layer 12, cells directly above where the laser light L was applied were dead; and in the region R2 without the to-be-irradiated layer 12, cells that were directly irradiated with the laser light L passing through the main body 11 survived.

In the case where the to-be-irradiated layer 12 comprises a photoacid generator, an acidic substance is generated in the partial area of the to-be-irradiated layer 12 irradiated with the laser light L and induces death of unwanted cells present directly above the partial area or induces detachment of these cells from the to-be-irradiated layer 12. In the case where the photoacid generator is a sulfonic acid derivative, the acidic substance thus generated is a sulfonic acid.

As described above, even in the case where each of the wavelength, the output, and the energy amount of the laser light L is set at such a level that does not kill cells upon direct irradiation, unwanted cells can still be adequately killed by the action of the to-be-irradiated layer 12.

In order to minimize the influence of heat on cells other than the unwanted cells, it is preferable that each of the wavelength, the output, and the energy amount of the laser light L to be applied to the to-be-irradiated layer 12 of the cell culture vessel 1 be adjusted to such a level that kills unwanted cells not instantly but after a certain period of time (for example, after several dozen minutes or after one to several hours) of irradiation with the laser light L.

Figure 7:
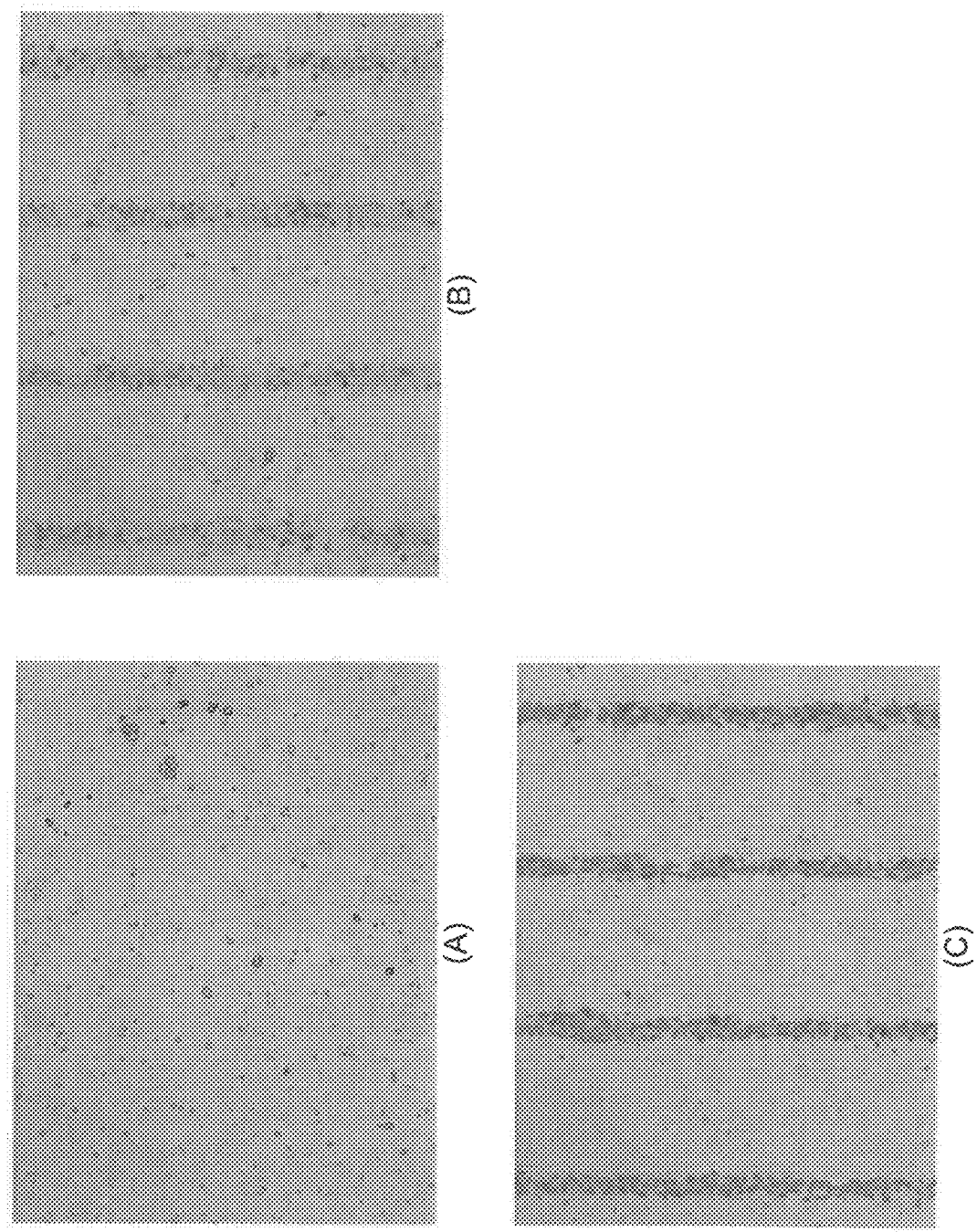
FIG. 7 comprises photographs showing the state of cells that have been killed not instantly upon laser irradiation but after a certain period of time of laser irradiation.

FIG. 7 shows the result of staining of dead cells with a trypan blue solution, which was conducted as follows: MDCK cells were cultured within the well 10 in the cell culture vessel 1 with the to-be-irradiated layer 12 disposed thereon; the continuous-wave laser L was discharged from the processing nozzle 33 toward the to-be-irradiated layer 12 at the bottom of the well 10; and after a certain period of time of the irradiation, the cells were stained. The wavelength of the laser L was 405 nm, the output of the laser L was 5 W, and the diameter of the laser beam L was 50 µm. In the example shown in the figure, the laser beam L was linearly moved at a rate of 1500 mm/second relative to the cell culture vessel 1, drawing one streak per every move and thereby drawing four streaks in total parallel to each other at 0.5-mm intervals. The area irradiated with the laser light L received energy of the laser light L of about 8.7 $J/cm^2$ per unit area. The to-be-irradiated layer 12 comprised a polymer that contained azobenzene as the pigment structure. FIG. 7(A) shows the result of trypan blue staining conducted 3 minutes after irradiation with the laser L, FIG. 7(B) shows the result of trypan blue staining conducted 56 minutes after irradiation with the laser L, and FIG. 7(C) shows the result of trypan blue staining conducted 122 minutes after irradiation with the laser L. These figures evidently show the following: after 3 minutes of irradiation, cells directly above the partial area irradiated with the laser light L were alive; after 56 minutes of irradiation, at least some of the cells directly above the partial area irradiated with the laser light L were dead; and after 122 minutes of irradiation, most of or all of the cells directly above the partial area irradiated with the laser light L were dead. Thus, it is possible to create a state where unwanted cells are alive right after irradiation with the laser light L and then are killed after a certain period of time of the irradiation. In this way, the influence of heat on cells other than unwanted cells, namely desired cells or tissues near unwanted cells, can be minimized.

Figure 8:
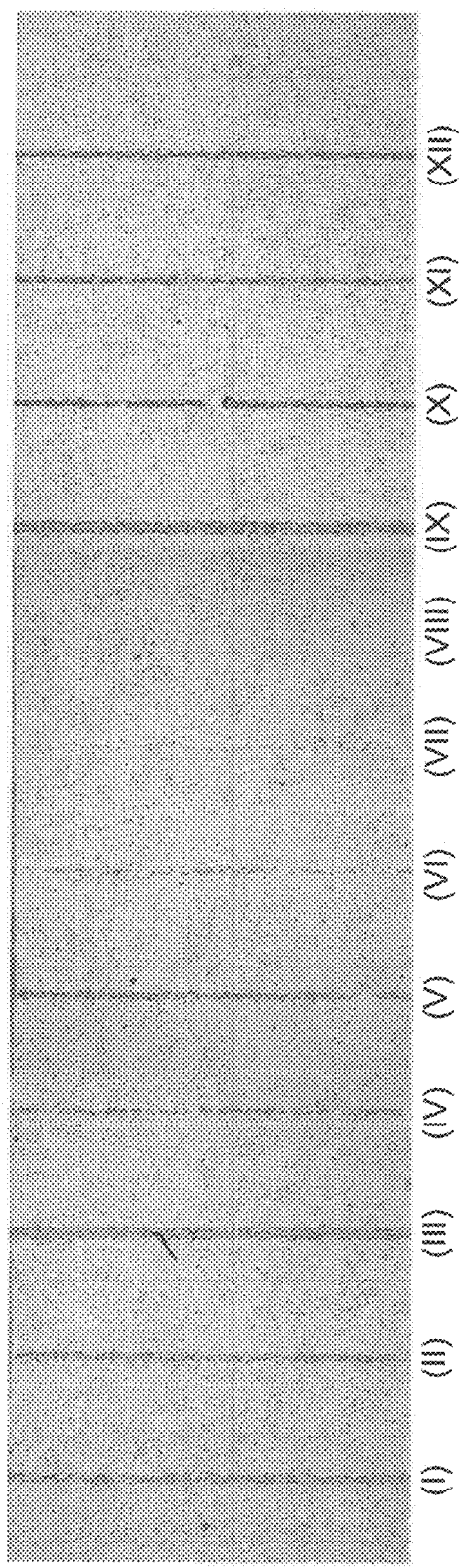
FIG. 8 is a photograph showing the correlation of the levels of the output of laser and the per-unit-area energy amount of laser with the state of cells (death or survival).

FIG. 8 shows the result of staining of dead cells with a trypan blue solution, which was conducted as follows: MDCK cells were cultured within the well 10 in the cell culture vessel 1 with the to-be-irradiated layer 12 disposed thereon; the continuous-wave laser L was discharged from the processing nozzle 33 toward the to-be-irradiated layer 12 at the bottom of the well 10; and after a certain period of time of the irradiation, the cells were stained. The wavelength of the laser L was 405 nm and the diameter of the laser beam L was 50 µm. The output of the laser L and the rate of moving the laser beam L relative to the cell culture vessel 1 were varied as follows:

(I) output of 5 W, movement rate of 2000 mm/second, energy density of about 6.5 $J/cm^2$
(II) output of 3.86 W, movement rate of 1600 mm/second, energy density of about 6.1 $J/cm^2$
(III) output of 2.44 W, movement rate of 1000 mm/second, energy density of about 6.2 $J/cm^2$
(IV) output of 1.89 W, movement rate of 800 mm/second, energy density of about 6.0 $J/cm^2$
(V) output of 1.6 W, movement rate of 640 mm/second, energy density of about 6.4 $J/cm^2$
(VI) output of 1.11 W, movement rate of 400 mm/second, energy density of about 7.1 $J/cm^2$
(VII) output of 0.86 W, movement rate of 320 mm/second, energy density of about 6.8 $J/cm^2$
(VIII) output of 0.4 W, movement rate of 200 mm/second, energy density of about 5.1 $J/cm^2$
(IX) output of 0.6 W, movement rate of 50 mm/second, energy density of about 30.6 $J/cm^2$
(X) output of 0.4 W, movement rate of 50 mm/second, energy density of about 20.4 $J/cm^2$
(XI) output of 0.4 W, movement rate of 50 mm/second, energy density of about 20.4 $J/cm^2$
(XII) output of 0.4 W, movement rate of 50 mm/second, energy density of about 20.4 $J/cm^2$ Irradiation with the laser beam L was conducted once for each condition. The to-be-irradiated layer 12 comprised a polymer that contained azobenzene as the pigment structure.

The amount of energy of the laser light L applied to a unit area irradiated with the laser light L increased as the output of the laser L increased and as the movement rate decreased. Even when the output of the laser L was low, the amount of energy that the partial area of the to-be-irradiated layer 12 irradiated with the laser light L absorbed was high when the movement rate is low, namely when the time period of irradiation with the laser light L of the partial area (which was to be irradiated with the laser light L) was long. As is evident from FIG. 8(VII) and FIG. 8(VIII), however, few or no cells in the irradiated area were killed at a low output of the laser L even when at least a certain amount of energy was given to the irradiated area. For ensuring that unwanted cells are killed by the laser L with a low output, it is required that the rate of moving the laser beam L be adequately low to make the amount of energy given to the irradiated area adequately high, as shown in FIG. 8(IX) to FIG. 8(XII). In contrast, when the output of the laser L is high, cells in the irradiated area can be killed even at a high movement rate.

As is evident from comparison between FIG. 8(IX) and any of FIG. 8(X) to FIG. 8(XII), the width or size of the area occupied by dead cells can be increased or decreased by controlling the output or the per-unit-area energy amount of the laser L. In other words, as the output and/or the per-unit-area energy amount of the laser L increases, the width or size of the area occupied by dead cells increases.

Figure 9:
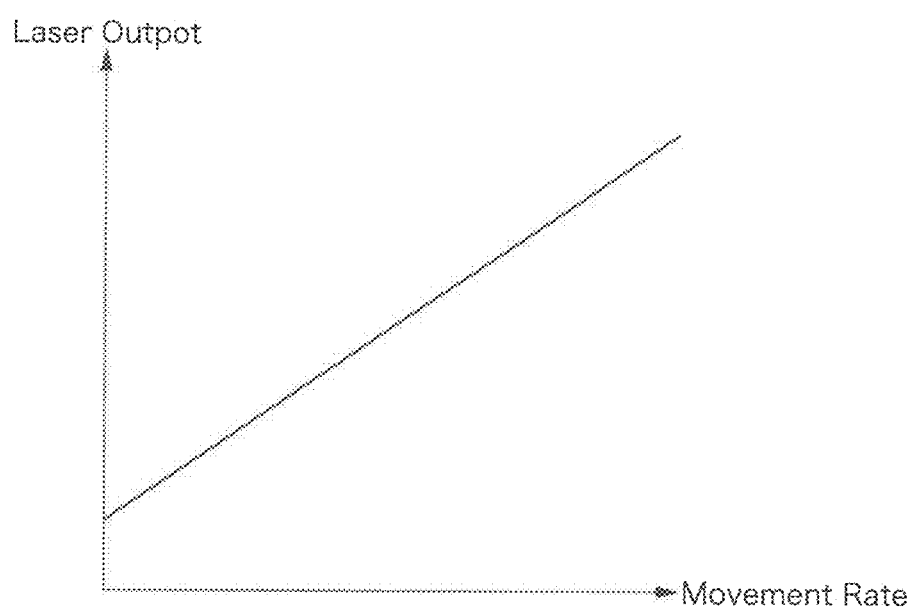
FIG. 9 is a graph conceptually showing suitable values of the laser movement rate and the laser output.

FIG. 9 conceptually shows the relationship between the rate of moving the laser beam L and the output of the laser L required for killing cells in an area having a certain width or size. When the rate of moving the laser L is higher or the output of the laser L is lower than the values plotted in the line shown in FIG. 9, the width or size of the area occupied by dead cells decreases. When the rate of moving the laser L is very high or the output of the laser L is very low, no cells are killed. In contrast, when the rate of moving the laser L is lower or the output of the laser L is higher than the values plotted in the line shown in FIG. 9, the width or size of the area occupied by dead cells increases, namely the influence of heat on desired cells or tissues adjacent to unwanted cells increases.

In addition, it is expected that the time period after irradiation with the laser L until the death of unwanted cells decreases as the output and/or the per-unit-area energy amount of the laser L increases.

Suitable conditions for the output and/or the per-unit-area energy amount of the laser L used in laser treatment are affected by the material, the thickness, and other characteristics of the to-be-irradiated layer 12 of the cell culture vessel 1. The amount of heat generation by a unit area of the to-be-irradiated layer 12 irradiated with the laser light L through absorption of energy of the laser light L is obtained by multiplying the amount of energy per unit area of the laser light L applied to the to-be-irradiated layer 12 by a factor of light utilization. The factor of light utilization refers to the rate at which a unit area of the to-be-irradiated layer 12 absorbs and utilizes energy of the laser light L. The factor of light utilization depends not only on the characteristics of (more specifically, the light absorbance by) the material of the to-be-irradiated layer 12 but also on the amount of a certain ingredient (per unit area of the to-be-irradiated layer 12) contributing to photo-thermal reaction in which heat is generated upon absorption of the laser light L. When the coating thickness of the material that forms the to-be-irradiated layer 12 of the main body 11 increases, the amount of the ingredient contributing to photo-thermal reaction increases accordingly, leading to an increase in the factor of light utilization of the to-be-irradiated layer 12 per unit area.

Such an increase in the factor of light utilization leads to an increase in the amount of heat generation by a unit area of the to-be-irradiated layer 12, facilitating cell death. In view of the circumstances above, it is required that the factor of light utilization by the to-be-irradiated layer 12 of the cell culture vessel 1 be considered and the output and/or the per-unit-area energy amount of the laser L suitable for killing unwanted cells be experimentally determined.

Figure 10:
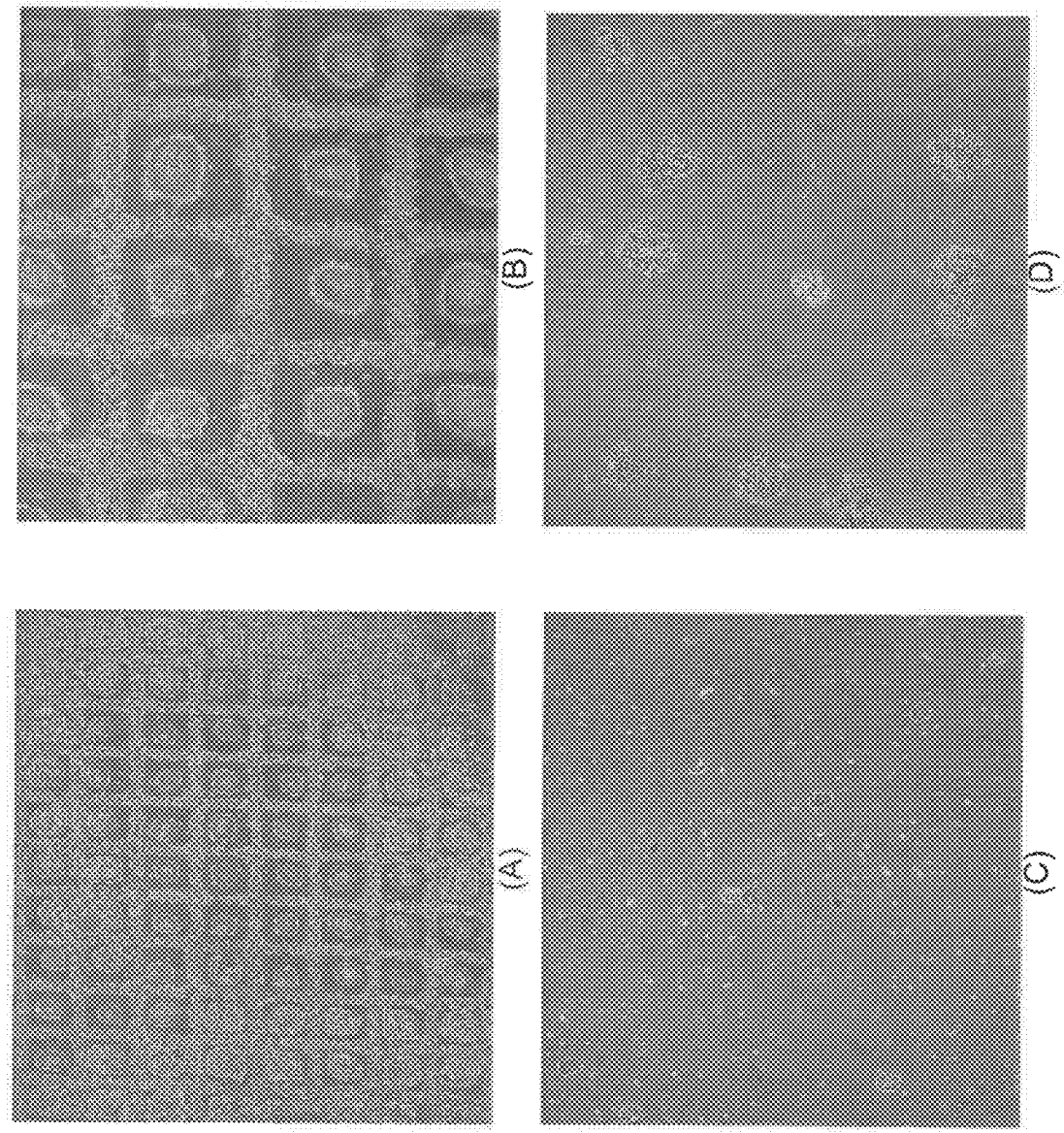
FIG. 10 comprises photographs of cell colonies divided into a plurality of portions by the cell treatment method according to the embodiment.
Figure 11:
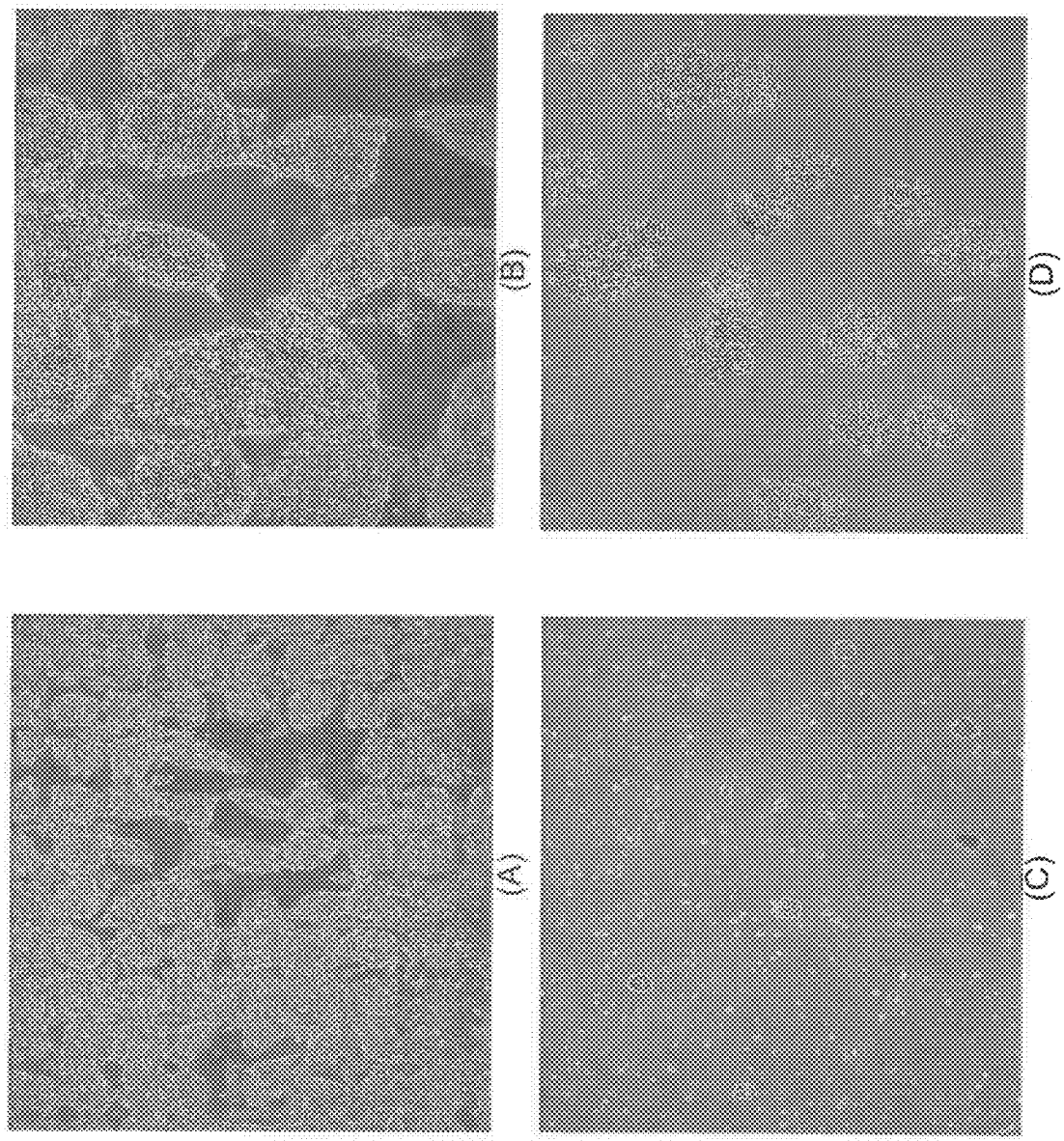
FIG. 11 comprises photographs of cell colonies divided into a plurality of portions by the cell treatment method according to the embodiment.

The laser processing machine and the cell culture vessel 1 according to this embodiment can be suitably used for dividing a cultured cell colony into a plurality of portions. FIG. 10 and FIG. 11 show the result of subculturing experiment, which was conducted as follows: on the cell culture vessel 1 comprising the to-be-irradiated layer 12 coated with Matrigel, which is an ECM, human iPS cells were cultured in a feeder-free manner; the resulting human iPS cells were divided into many cell clumps by laser treatment; the resulting cell clumps were transferred to a fresh culture medium for another round of proliferation. The wavelength of the laser L was 405 nm (the actual distribution of spectra ranged from 399 nm to 403 nm), the output of the laser L was 5 W, and the diameter of the laser beam L was 50 µm. In the example shown in the figure, the laser beam L was moved in a way that a grid was drawn on the cell culture vessel 1 and thereby unwanted cells on the to-be-irradiated layer 12 directly above the grid irradiated with the laser L were killed, to be followed by obtaining cell clumps consisting of cells other than the unwanted cells on the grid. In other words, cell colonies cultured on the cell culture vessel 1 were cut along the grid. The grid irradiated with the laser L corresponds to the boundary between clumps.

In the example shown in FIG. 10, the laser beam L was linearly moved at a rate of 1000 mm/second relative to the cell culture vessel 1, drawing one streak per every move and thereby drawing many streaks in total parallel to each other at 0.4-mm intervals to form the grid. The to-be-irradiated layer 12 comprised a polymer that contained azobenzene as the pigment structure. By applying the polymer to the upward-facing surface of the main body 11, namely the bottom of the well 10, at a density of 7 µg/cm$^2$, the to-be-irradiated layer 12 having an average thickness of 70 nm was formed on the bottom of the well 10. After irradiation with the laser L had been conducted and then a certain period of time required for killing unwanted cells had passed, an enzyme for detaching adhered cells from the surface of the to-be-irradiated layer 12 of the cell culture vessel 1 was added to the well 10 (shown in FIG. 10(A)). FIG. 10(B) is an enlarged view of FIG. 10(A). Cell clumps, namely clumps of living cells, detached from the cell culture vessel 1 and formed circles. FIG. 10(C) shows cell clumps obtained after laser treatment. FIG. 10(D) shows the state of the cell clumps a day after transferred to a fresh culture medium. As is evident from FIG. 10(D), the cell clumps cut and transferred from the cell culture vessel 1 started to grow successfully.

In FIG. 10(A) and FIG. 10(B), the cells along the grid are cells killed by laser treatment. In the example shown in FIG. 10, the output and/or the per-unit-area energy amount of the laser L may have been higher than the optimum levels. So, the output and/or the per-unit-area energy amount of the laser L may be decreased from these levels without hindering suitable cutting of cell clumps.

In the example shown in FIG. 11, the laser beam L was linearly moved at a rate of 500 mm/second relative to the cell culture vessel 1, drawing one streak per every move and thereby drawing many streaks in total parallel to each other at 0.4-mm intervals to form the grid. The to-be-irradiated layer 12 comprised a polymer that contained a thioxanthone-based sulfonic acid derivative having a thioxanthone backbone as the pigment structure and having a sulfonic acid as the acid precursor. By applying the polymer to the bottom of the well 10 of the main body 11 at a density of 200 µg/cm$^2$, the to-be-irradiated layer 12 having an average thickness of 2 µm was formed on the bottom of the well 10. After irradiation with the laser L had been conducted and then a certain period of time required for killing unwanted cells had passed, an enzyme for detaching adhered cells from the surface of the to-be-irradiated layer 12 of the cell culture vessel 1 was added to the well 10 (shown in FIG. 11(A)). FIG. 11(B) is an enlarged view of FIG. 11(A). Cell clumps, namely clumps of living cells, detached from the cell culture vessel 1 and formed circles. FIG. 11(C) shows cell clumps obtained after laser treatment. FIG. 11(D) shows the state of the cell clumps a day after transferred to a fresh culture medium. As is evident from FIG. 11(D), the cell clumps cut and transferred from the cell culture vessel 1 started to grow successfully.

In FIG. 11(A) and FIG. 11(B), unlike in FIG. 10(A) and FIG. 10(B), the cells killed by laser treatment are not distinctly visible and, instead, some of the cell clumps are observed to be not completely cut from but rather connected to each other. In the example shown in FIG. 11, the output and/or the per-unit-area energy amount of the laser L may have been lower than the optimum levels. So, the output and/or the per-unit-area energy amount of the laser L may be increased from these levels so as to obtain even better results.

The cell treatment method according to this embodiment is a method of killing specific cells from among a group of cells cultured in the cell culture vessel 1, the cell culture vessel comprising the main body 11 and the to-be-irradiated layer 12 attached to the main body, the to-be-irradiated layer 12 containing an ingredient capable of absorbing the laser light L upon laser irradiation, the group of cells being cultured on the surface of the to-be-irradiated layer 12, the method comprising:

applying the laser light L to a partial area of the to-be-irradiated layer 12 directly below the specific cells.

The cell treatment method above as well as use of the laser processing machine and the cell culture vessel 1 according to this embodiment can kill specific cells from among a group of cells cultured in the cell culture vessel 1 by quick and brief laser treatment. Raster scanning with the laser beam L across a certain region of (the to-be-irradiated layer 12 of) the cell culture vessel 1 can kill not only the unwanted cells that have not differentiated into desired cells, among cell colonies on the cell culture vessel 1, but also all the cells present within the region.

By applying the laser L to the partial area of the to-be-irradiated layer 12 directly below the boundary between any two portions of the group of cells cultured in the cell culture vessel 1, the group of cells can be divided into each portion. This technique is effective for easy collection of cell clumps having a uniform size, for subculturing.

The method disclosed in Patent Literature 1 takes a long time to kill target cells by irradiation with active energy rays. For example, treating an entire dish of a culture vessel having a diameter of 35 mm takes about 8 hours in calculation. In the cell treatment method according to this embodiment in which irradiating the cell culture vessel 1 with the laser beam L at a rate of 500 mm/second or higher can adequately kill unwanted cells, it takes only about 2.7 minutes to treat an entire dish of the cell culture vessel 1 having a diameter of 35 mm with the laser beam L having a diameter of 50 µm. In the case where the rate of moving the laser beam L is 1500 mm/second, it takes less than 1 minute for the treatment. This embodiment has made it possible to quickly kill unwanted cells in many cell treatment vessels in a certain period of time by irradiation with the laser L, greatly contributing to the production of a large amount of cells to be required in the near future for regenerative therapy.

The diameter of the laser beam L for irradiation of the cell culture vessel 1 can be as small as 50 µm or lower. So, a small cell of 20 µm or smaller, like a human iPS cell, can be adequately treated.

By irradiating the partial area of the to-be-irradiated layer 12 of the cell culture vessel 1 directly below the specific cells with the laser light L that has the right level of output or energy amount to kill the specific cells not instantly but after a certain period of time, the effect of heat on other cells near the specific cells can be minimized, leading to a further increase in the yield of desired cells or tissues.

The present invention is not limited to the embodiment that is described above in detail. In the embodiment above, target cells are killed by one-time irradiation of the partial area of the to-be-irradiated layer 12 of the cell culture vessel 1 directly below the specific cells with the laser light L that has the right level of output or energy amount to kill these cells not instantly (namely, not in about several minutes of irradiation with the laser light L) but after a certain period of time. In order to shorten the time period for killing target cells with a minimum effect of heat caused on the other cells, the laser light L having the right level of output or energy amount to kill the specific cells not instantly in one irradiation can be applied multiple times to the partial area of the to-be-irradiated layer 12 of the cell culture vessel 1 directly below the specific cells with the use of the same laser processing machine and the same cell culture vessel 1 as in the embodiment above.

FIG. 12 to FIG. 15 show the result of staining of dead cells with a trypan blue solution, which was conducted as follows: iPS cells were cultured within the well 10 in the cell culture vessel 1 having the to-be-irradiated layer 12 disposed thereon capable of generating heat upon irradiation with the laser light L; the continuous-wave laser L was discharged from the processing nozzle 33 toward the to-be-irradiated layer 12 at the bottom of the well 10; and as immediately as possible (practically, in about several minutes to about a dozen minutes required for staining), the cells were stained. During rinsing prior to trypan blue staining and during trypan blue staining, some of the cells detached from the well 10. The wavelength of the laser L was 405 nm, the output of the laser L was 1 W, and the diameter of the laser beam L was 50 µm. The to-be-irradiated layer 12 comprised a polymer that contained azobenzene as the pigment structure. In the example shown in the figure, the laser beam L was linearly moved at a rate of 100 mm/second relative to the cell culture vessel 1, drawing one streak per one or multiple moves and thereby drawing a plurality of streaks in total parallel to each other at 0.2-mm intervals. Regarding the number of times of moving the laser beam L, namely the number of times of irradiation with the laser light L, the example shown in FIG. 12 adopted one irradiation of the partial area directly below the target cells, to be immediately followed by trypan blue staining; the example shown in FIG. 13 adopted two irradiations of the partial area directly below the target cells, to be immediately followed by trypan blue staining; the example shown in FIG. 14 adopted four irradiations of the partial area directly below the target cells, to be immediately followed by trypan blue staining; and the example shown in FIG. 15 adopted six irradiations of the partial area directly below the target cells, to be immediately followed by trypan blue staining.

Figure 12:
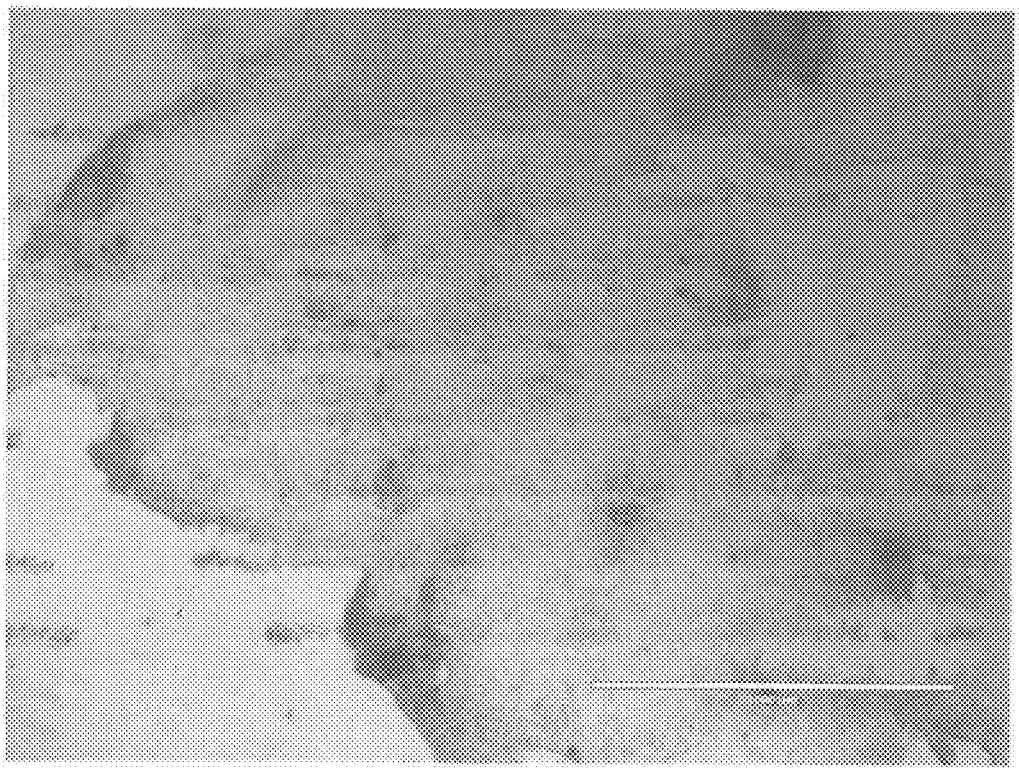
FIG. 12 is a photograph showing the state of cells (death or survival) observed after laser irradiation had been conducted once.
Figure 13:
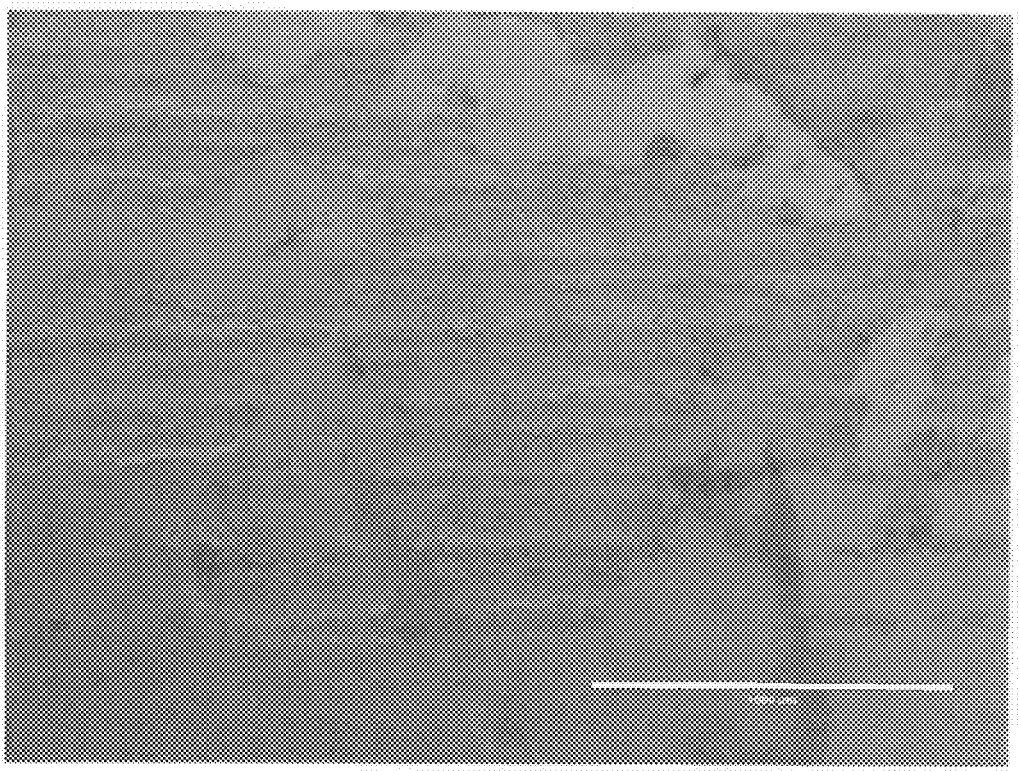
FIG. 13 is a photograph showing the state of cells (death or survival) observed after laser irradiation had been conducted twice.
Figure 14:
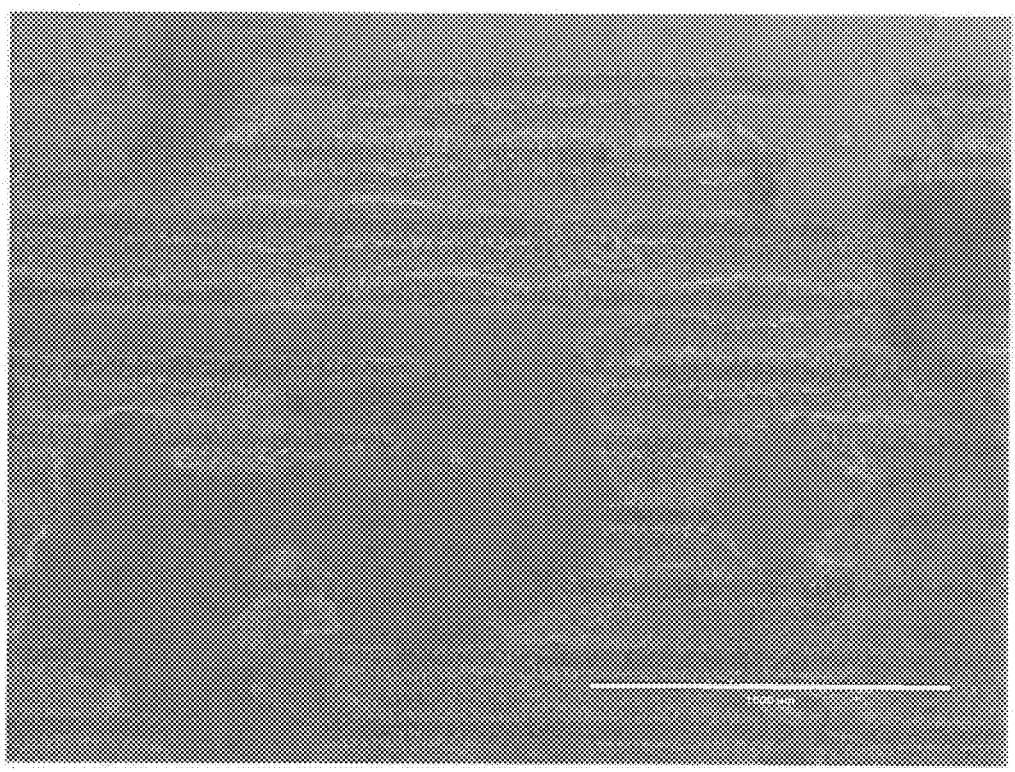
FIG. 14 is a photograph showing the state of cells (death or survival) observed after laser irradiation had been conducted four times.
Figure 15:
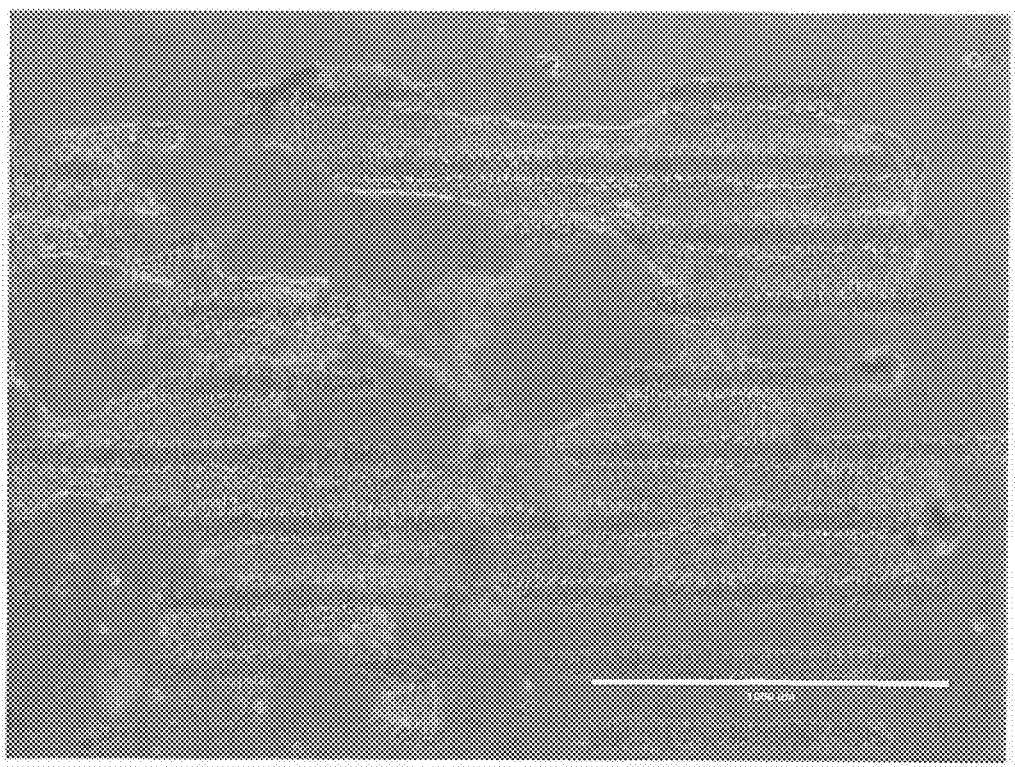
FIG. 15 is a photograph showing the state of cells (death or survival) observed after laser irradiation had been conducted six times.

In FIG. 12, only few cells were stained. This result indicates that cells directly above the irradiated area were alive after several minutes to a dozen minutes of one-time irradiation with the laser light L. In contrast to this, cells in FIG. 13 to FIG. 15 were stained. These results indicate that conducting irradiation with the laser light L twice or more than twice kills cells directly above the irradiated area only in a short period of time after the irradiation. It is also observed that when the number of times of irradiation with the laser light L increased from two to four, the intensity of the trypan blue staining observed right after irradiation with the laser L increased. This result indicates that the time period for killing cells is shortened as the number of times of irradiation with the laser light L increases. In particular, cells directly above the irradiated area were killed almost instantly after four irradiations of the laser light L. In FIG. 13 to FIG. 15, the width of the area occupied by stained cells was about 50 µm, which is approximately the same as the diameter of the laser beam L. As is evident from these results, by conducting multiple irradiations of laser light rays having the right output or the right amount of energy not to kill cells instantly, the time period for killing cells can be shortened with a minimum effect of heat on the other cells around the specific cells.

Comparison between FIG. 14 and FIG. 15 indicates that increasing the number of times of irradiation with the laser light L to five or greater does not change the effect of the irradiation to quickly kill target cells.

The wavelength of the laser L for laser treatment to kill unwanted cells is not limited to 405 nm. In the case where the laser L having a different wavelength is used, the to-be-irradiated layer 12 of the cell culture vessel 1 needs to be made by using an ingredient (particularly, a polymer) having a pigment structure capable of absorbing a light having that wavelength. In the case where a near-infrared laser L having a wavelength of 808 nm or 1064 nm is used, for example, a phthalocyanine (a phthalocyanine derivative or a near-infrared-absorbing phthalocyanine pigment) may be used. In this case, it is desirable that the phthalocyanine be immobilized on a side chain of the polymer via a chemical bond so that the phthalocyanine does not enter into cells. Use of a coordinated complex, even one capable of forming a polymer, should be avoided because such a complex may release a metal ion.

The diameter of the laser beam L may be smaller than 50 µm. By connecting an optical fiber having a small core diameter to the processing nozzle 33 and then making the laser light L emitted from the laser source 31 pass through the optical fiber to the processing nozzle 33, for example, the diameter of the laser beam L discharged from the processing nozzle 33 can be made to 25 µm or smaller and accordingly the amount of energy (energy density) of the laser L per unit area can be increased. In this case, even when the maximum output of the laser source 31 is not high, a considerable amount of energy can be applied to the area irradiated with the laser L, namely the partial area where unwanted cells are present.

Figure 16:
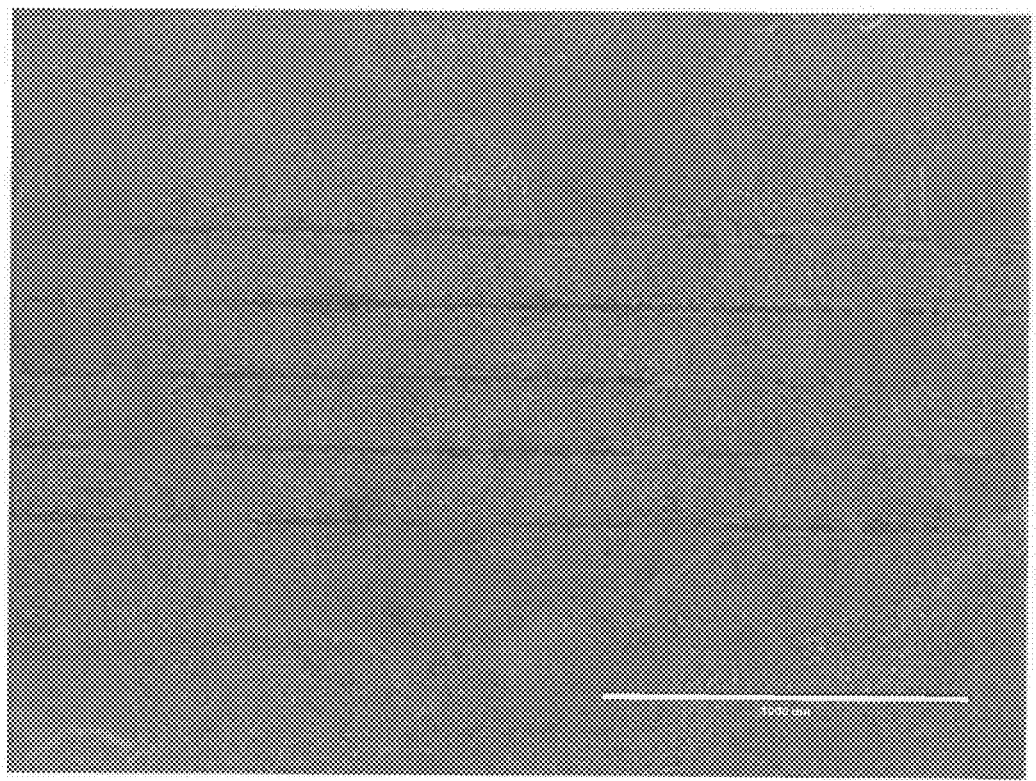
FIG. 16 is a photograph showing cells that have been killed by irradiation with a laser having a beam diameter as small as 20 μm.

FIG. 16 shows the result of staining of dead cells with a trypan blue solution, which was conducted as follows: iPS cells were cultured within the well 10 in the cell culture vessel 1 having the to-be-irradiated layer 12 disposed thereon capable of generating heat upon irradiation with the laser light L; the continuous-wave laser L was discharged from the processing nozzle 33 toward the to-be-irradiated layer 12 at the bottom of the well 10; and 1.5 hours after conducting the irradiation once, the cells were stained. The wavelength of the laser L was 405 nm, the output of the laser L was 0.18 W, and the diameter of the laser beam L was 20 μm. The to-be-irradiated layer 12 comprised a polymer that contained azobenzene as the pigment structure. In the example shown in the figure, the laser beam L was linearly moved at a rate of 300 mm/second relative to the cell culture vessel 1, drawing one streak per one move and thereby drawing a plurality of streaks in total parallel to each other at 0.2-mm intervals.

In FIG. 16, the width of the area occupied by stained cells was about 20 μm to about 25 μm, which is approximately the same as the diameter of the laser beam L. This result indicates that the effect of heat on other cells near the specific cells was successfully minimized. This width is equivalent to the collective width of about two iPS cells. By decreasing the beam diameter of the laser light L, the area to be occupied by dead cells can be decreased and therefore the yield can be enhanced. The cells in FIG. 16 were killed 1.5 hours after one-time irradiation with the laser light L. It is expected that the time period for killing target cells with the laser light L that has a beam diameter from 25 μm to 20 μm or smaller can be further shortened by conducting the irradiation of the single area multiple times.

The shape of projection of the laser beam L applied to the to-be-irradiated layer 12 is not limited to a spot or a circle. The shape of projection of the laser beam L may be a rod-like line beam extending toward a certain direction. The line-beam shape shortens the time period for raster scanning across a certain region of (the to-be-irradiated layer 12 of) the cell culture vessel 1.

In the embodiment above, the laser beam L is moved relative to the cell culture vessel 1 to draw a grid so as to cut cell clumps for subculturing. The path of movement of the laser beam L is not limited to a grid-shape. For example, the laser beam L may be moved relative to the cell culture vessel 1 so as to draw a hexagon mesh (or a honeycomb arrangement) consisting of a plurality of regular hexagons right next to each other on the to-be-irradiated layer 12, more specifically, so as to kill cells along the hexagon mesh. In this case, living cells remaining inside each hexagon are used as a cell clump.

In the embodiment above, the processing nozzle 33 configured to discharge the laser L toward the cell culture vessel 1 supported on the support 2 is mounted on the XY stage 4 and the processing nozzle 33 is moved in the X-axis direction and in the Y-axis direction. An alternative configuration may also be adopted where the support 2 supporting the cell culture vessel 1 is mounted on the displacement mechanism 4 such as the XY stage and the cell culture vessel 1 is moved in the X-axis direction and in the Y-axis direction. A yet another alternative configuration may also be adopted where one of the processing nozzle 33 and the support 2 is mounted on a linear-motor sliding platform or the like that can move in the X-axis direction and the other of these is mounted on a linear-motor sliding platform or the like that can move in the Y-axis direction, thereby the laser beam L discharged from the processing nozzle 33 being displaced in both the X-axis direction and the Y-axis direction relative to the to-be-irradiated layer 12 of the cell culture vessel 1.

The displacement mechanism 4 for displacing the target location of the laser L on the to-be-irradiated layer 12 of the cell culture vessel 1 may be a galvano scanner. As is well known, a galvano scanner is configured to turn a mirror that reflects the laser light L emitted from the laser source 31 with the use of a servo motor or a stepping motor, for example, allowing the mirror to quickly change the optical axis of the laser L. It should be noted that, in the case where a galvano scanner is used, the angle at which the optical axis of the laser light L crosses with the to-be-irradiated layer 12 of the cell culture vessel 1 cannot be maintained precisely constant. In the case where a semiconductor laser or the like is used as the laser source and the laser oscillated by the laser source is transferred to the galvano scanner through an optical fiber or the like, it is not easy to minimize the diameter of the laser beam L to be applied to the to-be-irradiated layer 12 or to minimize the scale of projection of the laser beam. For minimizing the diameter of the laser beam L or the scale of projection of the laser beam so as to enhance energy density, it is preferable to use a mechanism, such as the XY stage 4 or a linear-motor sliding platform, capable of moving the optical axis of the laser beam L in a direction parallel to the to-be-irradiated layer 12 of the cell culture vessel 1. By using a fiber laser as the laser source, the diameter of the laser beam L to be applied to the to-be-irradiated layer 12 or the scale of projection of the laser can be minimized.

A camera sensor for taking an image of cells in the cell culture vessel 1 may be disposed on the processing nozzle 33.

As the light source for providing light for taking an image of cells in the cell culture vessel 1, the laser light L discharged from the processing nozzle 33 may be used. In this case, the output of the laser L discharged from the processing nozzle 33 for irradiating the cell culture vessel 1 needs to be adequately lower than the output of the laser L to be applied to the cell culture vessel 1 for killing unwanted cells.

In the embodiment above, the to-be-irradiated layer 12 is formed by coating the bottom of the well 10 in the main body 11 of the cell culture vessel 1 with a polymer that is a material of the to-be-irradiated layer 12. However, it is difficult to coat the entire multidish-shape main body having a plurality of wells formed thereon with the polymer by a technique such as spin coating so as to form the to-be-irradiated layer. In view of this circumstance, an alternative configuration may also be adopted where an ingredient capable of generating heat upon irradiation with the laser light L is used to make a plate and the resulting plate is disposed on or attached to the bottom of each well in the main body to form the to-be-irradiated layer of the cell culture vessel. The plate may be made by applying a pigment capable of absorbing the laser light L to a sheet of a material, such as plastic or glass, that is transparent or light-transmissive to allow the passage of the laser light L. Alternatively, the sheet may be made with a material blend containing a pigment capable of absorbing the laser light L. Yet alternatively, the pigment-structure-containing polymer or the photoacid generator in the embodiment above may be used as the pigment capable of absorbing the laser light L.

In the embodiment above, the to-be-irradiated layer 12 is irradiated with the laser light L that is emitted from below the cell culture vessel 1 and then passes through the main body 11. An alternative configuration may also be adopted where the to-be-irradiated layer 12 is directly irradiated with the laser light L emitted from above, namely from the side of the surface of the to-be-irradiated layer 12 (without the laser light passing through the main body 11). In this case, it is not necessary for the main body 11 to be transparent or light-transmissive for allowing the passage of the laser light L. It is preferable that the focus of the laser light L for irradiation be adjusted not on cells on the to-be-irradiated layer 12 but on the to-be-irradiated layer 12.

For culturing iPS cells and other cells in the cell culture vessel 1, feeder cells may be concurrently used. The laser processing machine according to the present invention can also be used to kill feeder cells no longer required in the cell culture vessel 1.

Other specific configurations may be modified without departing from the scope of the present invention.

INDUSTRIAL APPLICABILITY

The present invention can be used to kill specific cells from among a group of cells cultured in a cell culture vessel.

REFERENCE SIGNS LIST

1: Culture vessel
11: Main body
12: To-be-irradiated layer
3: Laser irradiator
33: Processing nozzle
4: Displacement mechanism (XY stage)
5: Control module
L: Laser light

The invention claimed is:

1. A method of killing specific cells from among a group of cells cultured in a vessel comprising a main body and a layer attached to the main body, wherein the layer contains an ingredient capable of generating heat upon laser irradiation and the group of cells are cultured on the top surface of the layer, the method comprising applying a laser light to a partial area of the bottom surface of the layer by moving the laser light along a plane parallel to the partial area, wherein:
   the partial area of the layer irradiated with the laser light absorbs energy of the laser light and thereby generates heat that kills unwanted cells that are present directly above the partial area,
   the laser light does not instantly kill the specific cells upon irradiation,
   the laser light output is 5 W or less,
   the laser light wavelength is 380 nm or greater,
   the laser light moving rate is 2000 mm/sec or less, and
   the thickness of the layer is 10 mm or less.

2. The method according to claim 1, wherein the laser light is applied multiple.

3. The method according to claim 1, further comprising dividing the group of cells into a plurality of portions,
   wherein the laser light is applied to a partial area of the layer directly below a boundary between two of the portions.

4. The method according to claim 1, wherein the layer further comprises a polymer and the ingredient comprises an organic compound derivative.

5. The method according to claim 4, wherein the ingredient is selected from the group consisting of azobenzene, diarylethene, spiropyrane, spirooxazines, fulgides, leucopigments, indigo dye, carotinoids, flavonoids and quinoids.

6. The method according to claim 5, wherein the polymer comprises poly(methyl methacrylate) and the ingredient comprises azobenzene.

7. The method according to claim 4, wherein the polymer is selected from the group consisting of acrylic polymers, polystyrene polymers, polyolefin polymers, polyvinyl acetate, polyvinyl chloride, polycarbonate polymers, and epoxy polymers.

8. The method according to claim 1, wherein the top surface of the layer containing the ingredient is coated with an extracellular matrix.

9. The method according to claim 1, wherein the laser light is continuously moved along a plane which is parallel to a plane of the partial area.

10. The method according to claim 1, wherein the rate of moving the laser light is based on the output of the laser light.

11. The method according to claim 1, wherein the wavelength of the laser light is in a range of 380 nm to 808 nm.

12. The method according to claim 1, wherein an energy amount of the laser light is 25.9 J/cm$^2$ or less.

13. The method according to claim 1, wherein the laser light is applied by moving a processing nozzle including a lens for gathering the laser light prior to irradiation of the layer.

* * * * *